United States Patent [19]

Parsons

[11] Patent Number: 5,499,972
[45] Date of Patent: Mar. 19, 1996

[54] HYPODERMIC JET INJECTOR

[75] Inventor: James S. Parsons, Laguna Niguel, Calif.

[73] Assignee: Equidyne Systems, Inc., San Clemente, Calif.

[21] Appl. No.: 130,022

[22] Filed: Sep. 29, 1993

Related U.S. Application Data

[63] Continuation-in-part of Ser. No. 952,562, Sep. 28, 1992, abandoned.

[51] Int. Cl.$^6$ ..................................................... A61M 5/30
[52] U.S. Cl. ............................................. 604/68; 604/72
[58] Field of Search .............................. 604/68–72, 187, 604/218, 131, 133, 134, 135, 140, 141, 156, 157

[56] References Cited

U.S. PATENT DOCUMENTS

| | | | |
|---|---|---|---|
| 2,398,544 | 4/1946 | Lockhart | 604/68 |
| 2,737,946 | 3/1956 | Hein | 604/70 |
| 2,762,369 | 9/1956 | Venditty | 604/68 |
| 2,762,370 | 9/1956 | Venditty | 604/68 |
| 2,800,903 | 7/1957 | Smoot | 604/68 |
| 2,902,994 | 9/1959 | Scherer | 604/68 |
| 3,335,722 | 8/1967 | Lowry et al. | 604/69 |
| 3,688,765 | 9/1972 | Gasaway | 604/70 |
| 3,788,315 | 1/1974 | Laurens | 604/70 |
| 4,165,739 | 8/1979 | Doherty et al. | 604/68 |
| 4,378,015 | 3/1983 | Wardlow | 604/203 X |
| 4,518,385 | 5/1985 | Lindmayer et al. | 604/68 |
| 4,643,721 | 2/1987 | Brunet | 604/191 |
| 4,680,027 | 7/1987 | Parsons et al. | 604/68 |
| 4,722,728 | 2/1988 | Dixon | 604/68 |
| 4,874,367 | 10/1989 | Edwards | 604/72 |
| 4,913,699 | 4/1990 | Parsons | 604/68 |
| 5,026,343 | 6/1991 | Holzer | 604/68 |
| 5,062,830 | 11/1991 | Dunlap | 604/68 |
| 5,085,641 | 2/1992 | Sarnoff et al. | 604/134 |
| 5,190,523 | 3/1993 | Lindmayer | 604/72 |

*Primary Examiner*—C. Fred Rosenbam
*Assistant Examiner*—V. Alexander
*Attorney, Agent, or Firm*—Christie, Parker & Hale

[57] ABSTRACT

An ampule containing a liquid, e.g., a dose of medicine, connects to a hand-held portable power unit containing an energy accumulator which can be charged and then discharged by manual actuation of a trigger. Preferably the energy accumulator is a compressible spring which is charged by compressing it and discharged by releasing it. The discharging accumulator powers a thruster, preferably a rod, driving it against a plunger in the ampule. The driven plunger applies pressure to the liquid in the ampule and drives the liquid through a small tapered orifice having an open mouth. During an injection, the open mouth of the orifice is pressed against an injection site so that the liquid being forced through the orifice can hypodermically penetrate the injection site. The preferred compressible spring can be charged by forcing the thruster backward against the spring, compressing it to a point where a latching device catches it and holds it compressed. A carrying case automatically recharges the accumulator in this manner whenever the power unit is seated therein and the case's lid is closed. The trigger releases the latching device. Preferably there are two independent safeties to prevent inadvertent triggering of the power unit. One safety jams the trigger unless power unit has an ampule properly engaged, and a second safety for optional use is a slide that also jams the trigger. The ampules can be single-use, disposable items. An ampule loader is also disclosed.

22 Claims, 5 Drawing Sheets

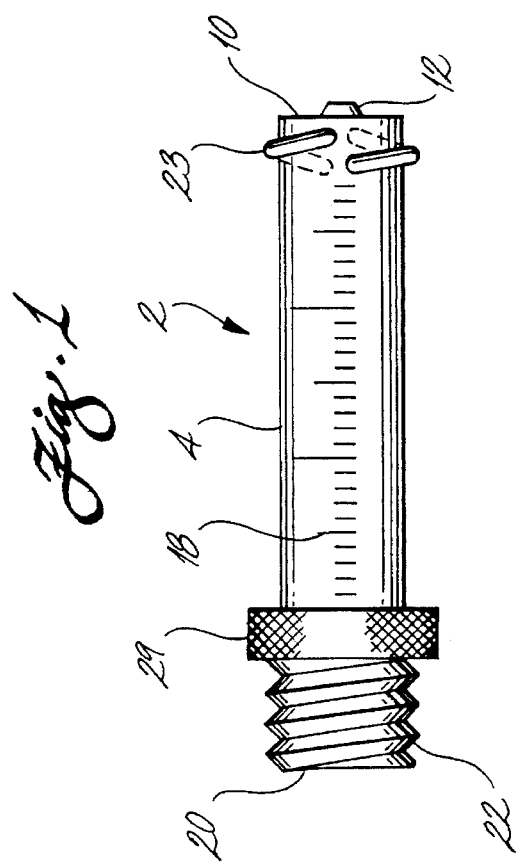
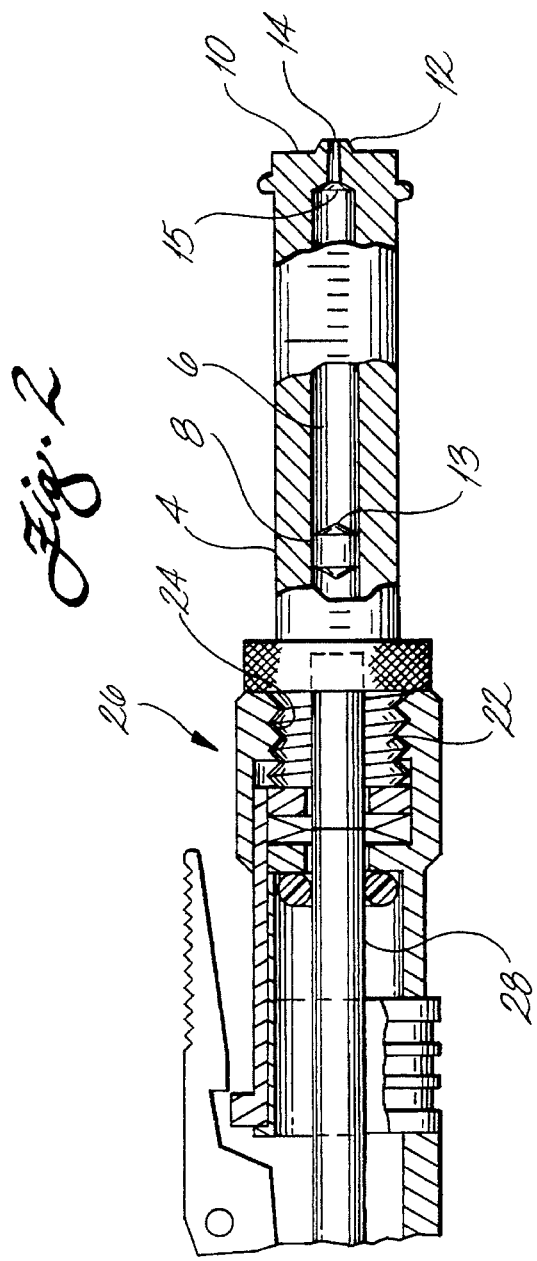

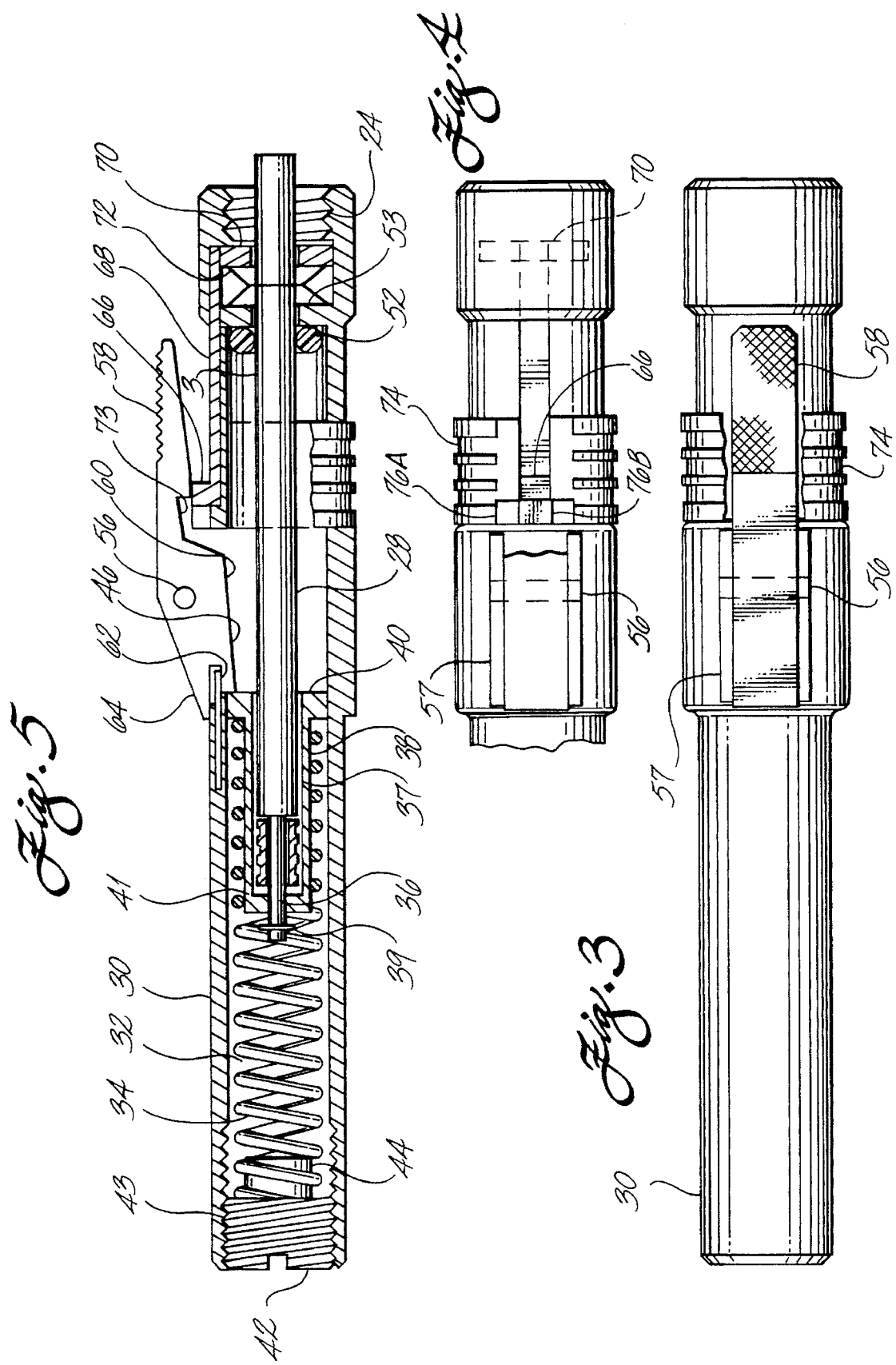

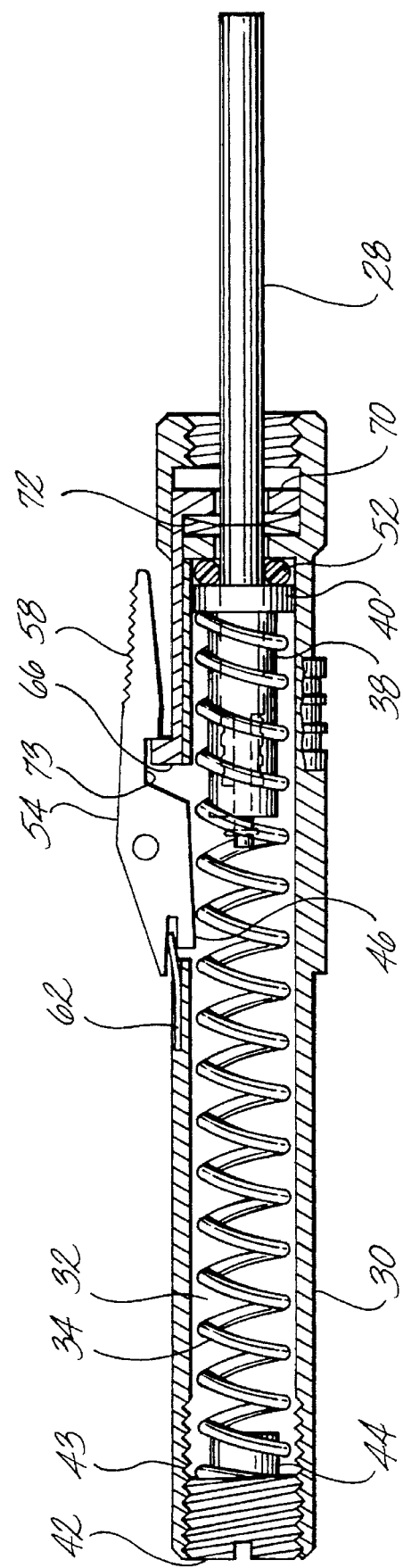

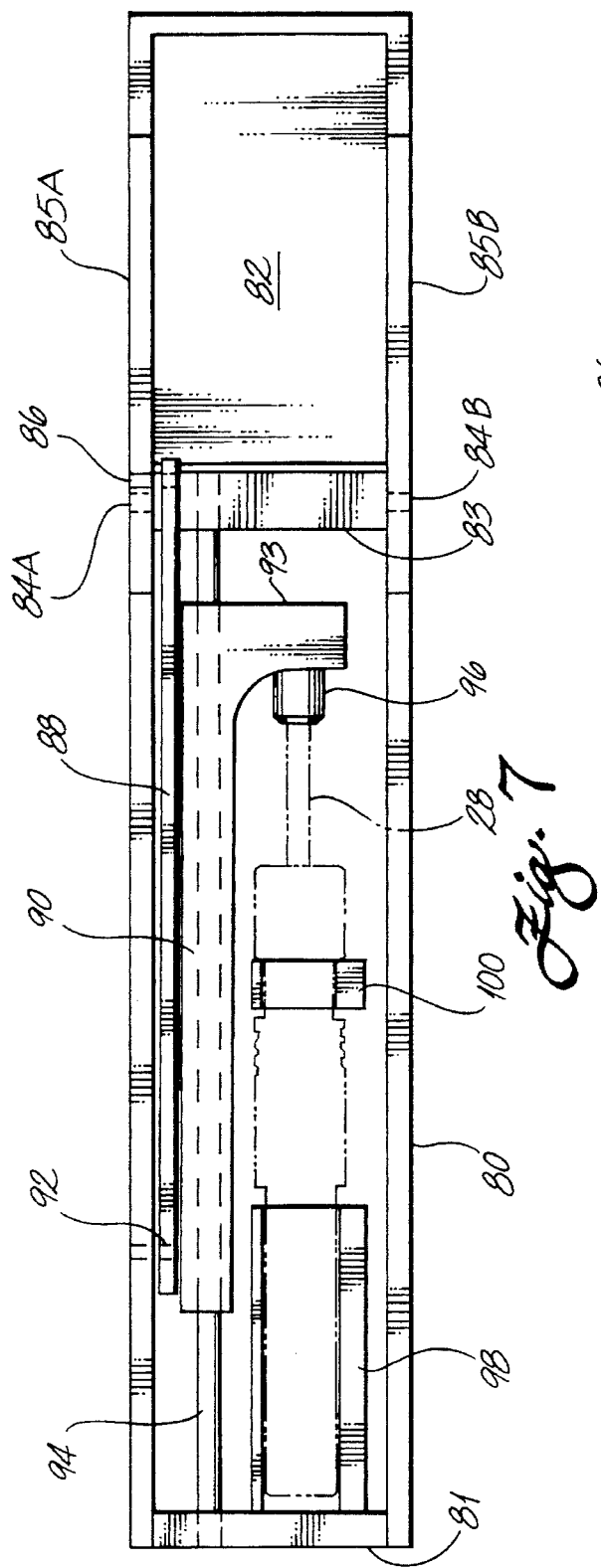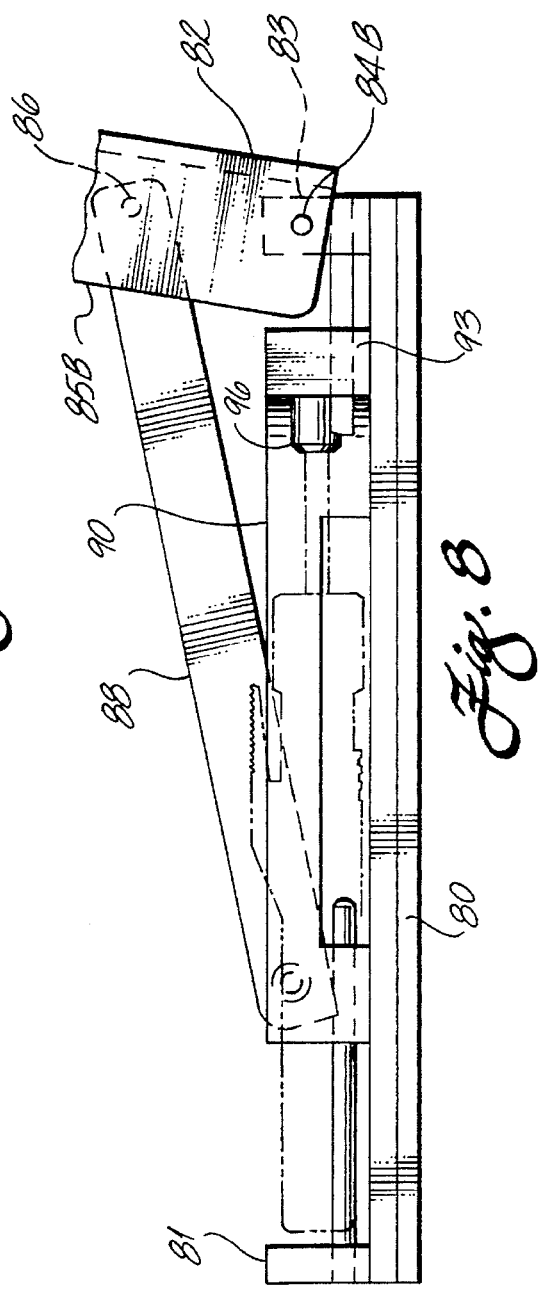

HYPODERMIC JET INJECTOR

This is a continuation-in-part of application Ser. No. 07/952,562 filed Sep. 28, 1992, entitled "HYPODERMIC JET INJECTOR", now abandoned, the entire disclosure of which is incorporated herein by reference.

BACKGROUND OF THE INVENTION

This invention relates in general to needle-less hypodermic drug delivery instruments using jet injection, and in particular to such instruments that are spring actuated.

This invention is a spring powered hypodermic delivery system using the well known jet injection principal to pass liquids such as medication through skin without the use of needles. This invention does not have these disadvantages.

Over a period of many years a variety of spring powered jet injectors have been proposed and patented, but they have all met with very limited acceptance due to such disadvantages as high cost and user inconvenience. In most cases these devices have incorporated means of cocking the power spring as an integral part of the primary instrument. The mechanism involved with the cocking function increases the size and cost of these instruments and has a negative effect on the convenience of application.

In the U.S. Pat. No. 4,874,367 by Edwards, the inventor proposes the elimination of the cocking mechanism on the instrument by relying on the user to reset the spring by simply pressing the exposed ram rod against a surface such as a table top, to force the ram into the cocked position. Edwards further suggests the use of a spring having a force of 20 pounds at full compression.

Such an instrument would have extremely limited application if any. In the first place, practical experience accumulated over several decades by a number of workers in the field of jet injection, clearly indicates the need for much higher spring tensions to accommodate the wide variations in human skin thickness, dose sizes and types of medication. Secondly, higher spring forces would render the manual cocking procedure quite impractical for most individuals. Even a 20 pound spring would eliminate most children and elderly persons from using the instrument. These population segments are the primary beneficiaries of jet injection.

The invention disclosed herewith separates the spring cocking function from the injector instrument but provides an effective spring compression mechanism in a companion carrying case. The carrying case serves as a protective enclosure for the injector and at the same time automatically cocks the instrument when the lid of the case is closed. After closing the lid the injector remains in the case until needed, at which time the lid is opened and the instrument removed. It will then automatically be in the cocked condition and with an interlocking safety on.

The power unit of the system has a spring driven rod, which slides into a disposable medication ampule and forces the liquid through a small orifice to make the injection. If the trigger were actuated with the ampule not in place, the rod could inflict serious injury to the operator. This eventuality is rendered impossible by the provision of an interlock mechanism between the ampule attachment point and the injector trigger. This mechanism inserts a mechanical block under the trigger unless the ampule is in place and fully seated, thus preventing the inadvertent release of the rod.

A second level of safety is also provided at the discretion of the user. This second safety feature is engaged by moving a sliding sleeve forward, which also restricts the actuation of the trigger when the ampule is in place but the user does not wish to make the injection immediately. Both of these safety features are mandatory if the system is to be acceptable to the medical profession.

This system is dramatically smaller than conventional jet injectors, and can be as small as 3¾ inches long by ⅝ of an inch in diameter. Its cost to a user is correspondingly lower, e.g. one-tenth or less the cost of conventional instruments. For user comfort it incorporates means for adjusting penetration depth. Moreover, its simplicity is enhanced because it does not incorporate typically bulky means for resetting the instrument as an integral part. This function is accomplished by a separate component which is the subject of a related patent application. This separation helps account for the extreme simplicity of the injector and its small size.

This system comprises both permanent and disposable components cooperating in a novel design having simplicity in both structure and function resulting in low user costs.

This system is very suitable for the administration of a wide variety of drugs in clinical settings or in physicians' offices when a subcutaneous or shallow I.M. shot is appropriate. A primary application, however, is the self-administration of insulin by diabetics for which use this system is well suited.

SUMMARY OF THE INVENTION

An object of this invention is to provide a needle-less hypodermic injector system having a lower cost-per-shot than was heretofore possible and the smallest practical component size while providing the comfort and efficacy of needle-less injectors.

A further object of this invention is to provide a hypodermic jet injector system that is dramatically smaller than conventional jet injectors.

A further object of this invention is to provide a hypodermic jet injector system that does not incorporate means to reset the instrument as an integral part.

A further object of this invention is to provide a hypodermic jet injector system that uses a disposable ampule both as the medicine container and as the only part that need come in contact with an injectee's skin.

A further object of this invention is to provide a hypodermic jet injector system that has an integral means for adjusting penetration depth and/or a user's comfort level.

A further object of this invention is to provide such a drug delivery system with a high degree of operator safety.

These and other objects which are expressly or impliedly set forth hereinafter are achieved by an injector system of which a power unit is preferably a non-disposable component and of which a cooperating medication ampule can be a disposable component. The ampule can be available to a user pre-sterilized in an individual plastic package. It can be filled by a user from a conventional syringe cartridge using an ampule loader according to this invention. Alternately the ampule can be available pre-filled with the proper medication at proper doses. The ampule is attached to the power unit and an injection is made at a selected skin site, after which the ampule is removed and can be discarded. The ampule incorporates a plunger to discharge the medication through a very small orifice at a forward end which under high pressure forms the jet of fluid which penetrates the skin. The ampule is transparent and has an accurate scale against which the user can set the desired dose of medication. The power unit is powered by a mechanical spring that is released by a finger operated trigger having at least two safety mechanisms to prevent inadvertent release of the spring. A forward end of the power unit has a threaded recess to which the disposable ampule is attached prior to injection. When the spring is released a thrust rod lunges forward into the ampule propelling the plunger forward to discharge the medication. A power unit carrying case also serves to cock the power unit, i.e. compress the spring. With the single-use, disposable, needle-less ampule, the risks of infection are minimized and the contribution to dangerous medical waste greatly reduced.

BRIEF DESCRIPTION OF THE DRAWINGS

FIG. 1 is a plan view of a medication ampule according to this invention.

FIG. 2 is a partial cross-sectional view illustrating cooperation between an ampule as illustrated in FIG. 1 and a power unit.

FIG. 3 is a plan view of the power unit.

FIG. 4 is a partial plan view of the power unit with a trigger lever broken away.

FIG. 5 is a cross-sectional view of a cocked power unit taken along line 5—5 of FIG. 3.

FIG. 6 is a cross-sectional view of an un-cocked power unit taken along a longitudinal median.

FIG. 7 is a plan view of an opened reset box.

FIG. 8 is a cross-sectional view of the reset box taken along line 7—7 of FIG. 7.

DESCRIPTION OF THE PREFERRED EMBODIMENT

Figure 9:
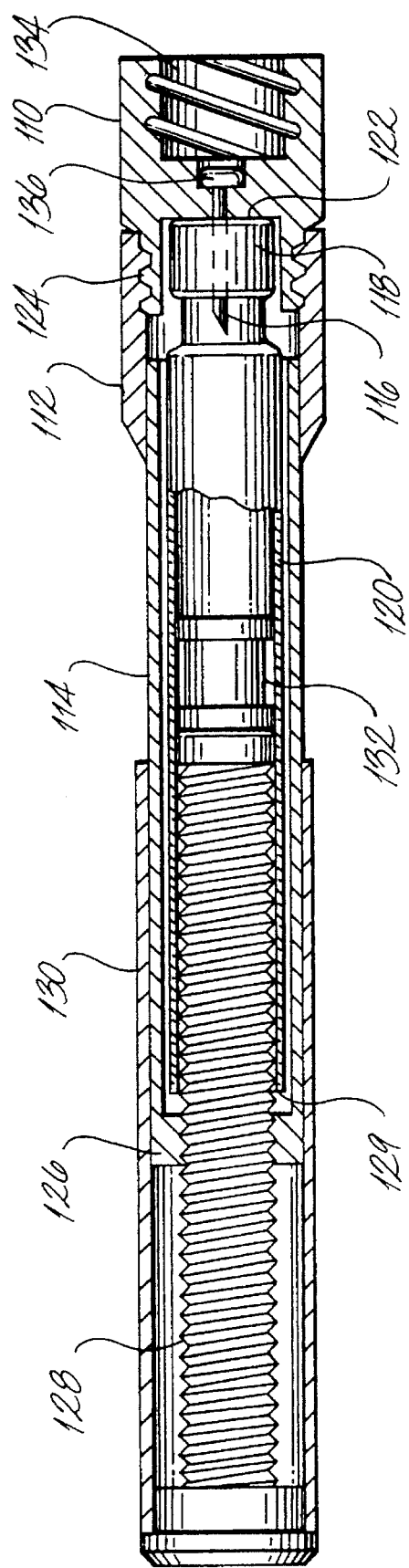
FIG. 9 is a cross-sectional view of a device for loading medication into an ampule as illustrated in FIG. 1.

Referring to FIGS. 1 and 2, an ampule, generally designated 2, is illustrated as having an elongated cylindrical shell 4 defining a longitudinal, concentric hollow cylinder 6. Within the hollow cylinder is a plunger 8 which snugly but slidably fits therein forming a high pressure seal around the entire interface of the plunger with the wall of the hollow cylinder. In operation, a "front" end 10 of the ampule comes in contact with skin into which medication is to be injected. (It should be noted that the end 10 of the ampule is arbitrarily designated the "front" end for reference purposes only, and other location terms used herein concerning the ampule, such as "forward", "rear", "rearward" and the like are merely relative to said front end.) Generally the front end 10 is flat except for a centered frusto-conical protrusion 12. This protrusion, when pressed against the skin, tends to form a pocket which is advantageous during the injection process. Centrally defined by the protrusion and the front end is a open tapered orifice 14 which communicates with the hollow cylinder 6 and has a common longitudinal axis therewith, but which is much smaller in diameter. It has been found that an inner diameter of approximately 0.006 inches for the mouth of the orifice is generally suitable for the purposes of this invention. As illustrated the plunger has a slightly tapered front end 13 which generally conforms to a tapered recess 15 defined by the front end wall of the hollow cylinder. The rear end of the plunger has an identical taper for simplicity of installation.

In operation, a liquid (generally medication) is inserted, in proper dosage, into a chamber which is that portion of the hollow cylinder between the ampule front end and the plunger, and the front end of the ampule is pressed against an injection site. The plunger is then driven forward by a linearly applied force and converts this force to pressure on the liquid sufficient to cause the liquid to leave the chamber via the orifice at such a velocity that it can be hypodermically injected at the injection site. The tapered recess 15 preceding the orifice funnels the liquid into the orifice, and the conforming tapered front end 13 of the plunger ensures that all the liquid is ejected.

A preferred method of inserting liquid into the ampule chamber is to mate the front end of the ampule with a device that can communicate liquid under pressure through the front end orifice into the chamber without allowing ambient gas to enter to chamber, the pressure being sufficient to drive the frictionally resisting ampule plunger backward to accommodate (within the capacity of the hollow cylinder with the plunger therein) the amount of liquid being inserted.

Referring again to FIGS. 1 and 2, preferably the ampule shell 14 is transparent to permit viewing of the amount of medication therein, and further has dosage scale graduations 18 along its length with the plunger as a marker for setting a proper dose.

Figure 10:
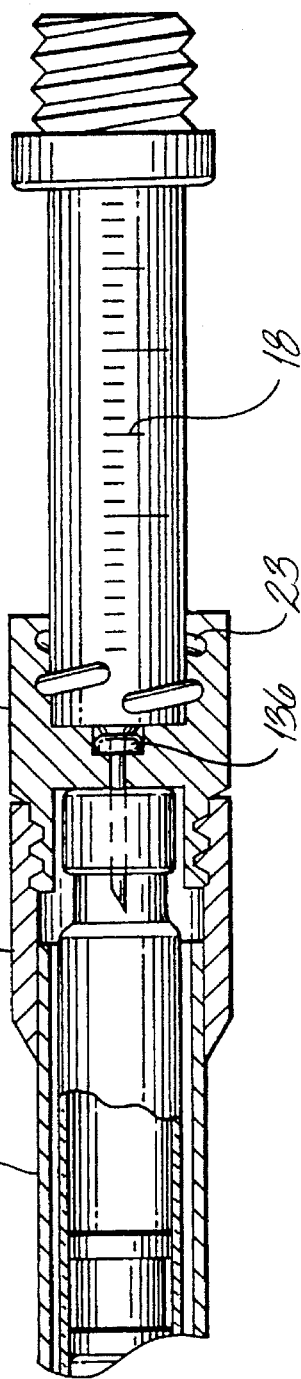
FIG. 10 is a partial cross-sectional view the device of FIG. 9 with an ampule attached thereto.

Referring again to FIGS. 1 and 2, the hollow cylinder 6 is open at the rear end 20 of the ampule where there are external male threads 22 for engaging a corresponding female threaded opening 24 defined by a head, i.e. a "front" end, of a power unit, generally designated 26. (It should be noted that said end of the power unit is arbitrarily designated the "front" end for reference purposes only, and other location terms used herein concerning the power unit, such as "forward", "rear", "rearward" and the like are merely relative to said front end.) The power unit has therein a thrust rod 28 which in operation is thrust forward from the power unit into the ampule's hollow cylinder 6 to impact the plunger 8 and drive it forward. The thrust rod of the power unit is the means by which force is linearly applied to the plunger to drive it forward to propel the medication out of the ampule's front end orifice 14. The plunger is in effect a movable wall of the chamber which when driven forward forcefully reduces the volume of the chamber. The ampule also has a flat annular ridge 29 projecting therefrom which may be knurled. This ridge provides a finger gripping surface by which a user can screw the ampule into a power unit, via the male threads 22, or for engaging it with a device (such as illustrated in FIGS. 9 and 10) that can communicate liquid under pressure into the ampule through the ampule's front end orifice 14 via front end coupling means 23 which preferably comprises LUER threads common in the art of medicine delivery instruments.

Referring to FIGS. 5 and 6, the power unit is illustrated as having an elongated cylindrical housing 30 defining a longitudinal channel 32 in which is disposed a coiled spring 34, the thrust rod 28, and means for transferring linear force exerted by the spring, when expanding, axially to the thrust rod. Preferably the longitudinal axes of the spring and the thrust rod are collinear. A rear length 36 of the rod has a diameter smaller than the remaining, forward length 37 of the rod, and annular to most of this rear length and part of the forward length is a sleeve 38 having an inner diameter slightly larger than the forward length of the rod and an outer diameter slightly smaller than the inner diameter of the coiled spring 34. The sleeve occupies an annular space between the forward length of the thrust rod and the coiled spring, keeping the rod and spring aligned. At the front end of the sleeve is an outwardly projecting, annular flange 40 which presents a shoulder against which a forward end of the spring abuts. At the rear end of the sleeve is an inwardly projecting, annular flange 41 which essentially closes the sleeve except for an opening through which the rear length 36 of the thrust rod extends. In the annular space between the sleeve 38 and the rear length 36 of the rod is an elongated annular shock absorber 48. The rear end of the coiled spring abuts a means for adjusting the compression force of the spring. Preferably this adjustment means is a screw 42 which engages female threads 43 at the rear end of the channel 32. The screw closes the rear end of the channel and is used to selectively shorten or lengthen the channel. The rear end of the spring abuts the foot of the screw and the front end of the spring abuts the annular flange 40. A stud 44 projecting from the foot of the screw keeps the abutting end of the spring centered. The sleeve is kept in relation to the rod by a retaining ring 39 secured at the end of the rear length 36.

Referring again to FIGS. 5 and 6, as illustrated the adjustment means is a set screw, but any means which can selectively shorten or lengthen the channel in which the compression spring is confined can be used. Moreover a finger turnable screw, e.g. a screw having a knurled knob or flange around its head, can be used in place of the set screw without departing from the scope of this invention.

Referring to FIG. 5, the coiled spring 34 is illustrated in a compressed state. It is held in this compressed state by a latch 46 which protrudes into the channel 32 and catches the sleeve's front flange 40. When the latch is removed from obstructing movement of the sleeve, the coil acting against the sleeve will cause it to move forward. The sleeve's rear flange 41 will impact and act against the shock absorber 48 which in turn will act against a shoulder created by the difference in diameters between the rear and forward lengths of the rod 28. In this way, the force of the expanding spring is linearly exerted against the thrust rod. Preferably the shock absorber is made from resilient material such as rubber or rubber-like material. The expanding spring will drive the rod forward until the forward face of the sleeve 38 encounters a cushion 52 affixed to a wall 53 at the front extremity of the channel 32. As illustrated, this cushion is in the form of an "O" ring having a hollow center to allow passage of the rod therethrough. The front wall 53 of the channel defines a passageway through which the rod can likewise extend. Thus when the ampule is engaged with the power unit, there is a continuous passageway through the cushion 52, through the front wall of the channel 32, and into the ampule so that the rod can drive the ampule plunger 8.

The cushion 52 at the front wall 53 of the channel cushions the impact of the sleeve 38 against the wall. It suppresses the noise of the collision and prevents thumping. It also reduces wear on the instrument. The cushion can be made from rubber or any other suitable resilient, energy-absorbent material.

The shock absorber 48 softens the impact of the rod against the ampule plunger. This is especially useful for ampules containing small doses of medicine. In such cases the plunger is further forward in the ampule and therefore the stroke of the rod (the distance the rod travels before encountering the plunger) is greater. With a greater stroke the rod develops a greater velocity and hits the plunger harder. The shock absorber momentarily absorbs some of the energy being delivered by the rod sleeve 38 when the rod first hits the plunger and thus it softens the impact on the plunger. This keeps the initial instantaneous pressure applied to the medicine at a level safely within ampule structural limits.

Referring again to FIGS. 5 and 6, when the power unit is un-cocked, the sleeve's front flange 40 is forward of the latch 46. In order to cock the power unit, the thrust rod is pushed backward, by any suitable means (such as illustrated in FIGS. 7 and 8), until the sleeve's front flange is caught by the latch. Preferably the latch is a tongue at the end of a lever 54 which pivots about a pin 56 journaled in a clevis 57 affixed to the housing 30, the opposite end of the lever being a trigger 58 having a flat knurled surface and disposed to be finger actuated. As the rod is being pushed backward during a cocking operation, the front flange 40 encounters a beveled surface 60 on the underside of the lever, the underside of the latch being part of the beveled surface. As the rod is pushed further rearwardly, the sleeve flange rides against the beveled surface and causes the latch to pivot out from the channel 32 to at least an extent necessary to permit passage of the sleeve flange 40. As the latch pivots out of the channel it bends a normally flat leaf spring 62 which projects over a top side of the latch. Once the sleeve's front flange is pushed back beyond the beveled surface, the resilience of the leaf spring causes the latch to re-enter the channel and present an obstruction to forward movement of the sleeve. A stop 64 prevents the latch end of the lever from pivoting too far into the channel. Forcing the rod backward causes the coiled spring to accumulate energy which is stored in the spring until it is released.

Referring again to FIGS. 5 and 6, the coiled spring 34 can be released by pressing down on the trigger 58 which causes the lever to rotate about pivot pin 56 and move the latch 46 out the channel 32 and out of the way of the sleeve 38. To prevent inadvertent triggering of the power unit, there are two safety mechanisms. As illustrated, one safety mechanism is automatically in place whenever the power unit does not have an ampule engaged thereto. This safety will not allow the power unit to be triggered until an ampule is fully screwed into the head of the unit. This safety has a blocking means which jams the trigger to prevent downward rotation thereof. This blocking means is a protrusion 66 which is normally lodged between the trigger and the housing 30. The protrusion is connected to one end of a movable arm 68, the other end of which is connected to a movable ring wall 70 which defines a central opening through which the rod extends. This ring wall is spaced from and disposed forward of the relatively immovable wall 53 at the front extremity of the channel 32. Between the relatively immovable wall 53 and the movable wall 70 is a compressible spring 72, such as a star washer. Normally the compressible spring biases the ring wall forward enough for the protrusion 66 to jam the trigger thereby preventing actuation thereof. However whenever an ampule is fully screwed into the threads 24 of the power unit, the rear end of the ampule pushes the ring wall back far enough to remove the protrusion as an obstruction to movement of the trigger, and thereby releasing this first safety. As illustrated, the ampule pushes the protrusion back until it aligns with a recess 73 under the trigger, which alignment allows the trigger to be sufficiently actuated to release the thrust rod, i.e. fire the power unit. Thus by this first safety, a user cannot release the thrust rod, and cause possible injury to self or others, without having an ampule fully engaged with the power unit.

Referring again to FIGS. 3–6, as illustrated the second safety mechanism is a ring 74 annular to the housing 30, which ring can slide back and forth along the housing between two extremes. At a forward extreme (not shown), the ring's forwardmost range of movement, the ring has a pair of projections, 76A and 76B, that are lodged between the housing and the trigger so as to prevent movement of the trigger toward the housing. At this forward extreme, the projections are generally aligned with, and straddle, the protrusion 66 of the first safety when in its normal position. Thus when the ring is at this forward extreme, the projections will jam the trigger and prevent actuation of the same. A stop (not shown) prevents the ring from moving forward beyond the first extreme. At the ring's rear extreme (illustrated in FIG. 4), the projections, 76A and 76B, are beneath the trigger recess 73 and do not prevent actuation of the trigger. This safety is for optional use as compared to the first safety which can only be disengaged when an ampule is properly in place.

In this invention, the trigger is disposed on the side of the power unit, and this has distinct advantages over other locations for the trigger. With this invention, a user can apply pressure to an injection site by, for example an index finger, and independently adjust pressure on the skin without inadvertently triggering the unit. Moreover, a person administering an injection to another person can more conveniently hold and trigger the unit.

Referring to FIG. 6, in an uncocked or fired power unit the trigger 58 is in a generally depressed state with the first safety's protrusion 66 captured in the trigger's recess 73. It is held that way because the coiled spring 34 blocks the latch 46 from fully re-entering the channel 32, and so the lever 54 is blocked from rotating (counter-clockwise per the illustration) sufficiently for the trigger to return to its firing position (as illustrated in FIG. 5) and for the first safety's protrusion to be released. When the power unit is being cocked by pushing the rod back until the sleeve's front flange 40 is pushed back beyond the latch, the latch is free to fully re-enter the channel under the influence of the leaf spring 62. This re-entry causes the trigger to rise and release the first safety's protrusion. Thus at essentially the same moment the power unit is cocked, the first safety engages.

As an additional advantage of this invention, the power unit and ampule combination can be designed to administer very small doses of medication by simply providing ampules with a smaller internal diameter and a power unit having a correspondingly smaller diameter thrust rod, while keeping all outer dimensions constant. The smaller ampule internal diameter results in an extended dosage scale providing greater accuracy in setting the dosage. This is a highly desirable feature in such applications as delivering small doses of medication to children.

Referring to FIGS. 7 and 8, illustrated is a power unit carrying case which automatically cocks the power unit while closing the case. The case, which can be called a "reset box," has an elongated rectangular base 80. At one end of the base is a narrow wall 81 projecting up from the base. A cover 82 is hinged to an opposite narrow wall 83 also projecting up from the base, the connection is by means of hinge pivots 84A and 84B. The cover has side walls, 85A and 85B, projecting therefrom, and when closed the cover forms the top and the two long sides of the rectangular case with the narrow walls closing the case at its ends. Pivotally connected to a cover side wall 85A by a linkage pivot 86 is one end of a linkage bar 88. The opposite end of the linkage bar is pivotally connected to an elongated shuttle member 90 also by a linkage pivot 92. The shuttle member slides back and forth, driven by the linkage bar, along a slide bar 94 which extends from and between the case's end walls and is parallel to the long axis of the case. Projecting from the shuttle member at an end closest to the cover hinge is a leg 93 and affixed to the leg is a pillow 96. Along side the shuttle's path and affixed to the base is a cradle 98 adapted to seat a rear portion of the power unit. A neck cradle 100 also affixed to the base is adapted to seat that portion of the power unit immediately behind the unit's head. This neck cradle ensures that the second safety (74 of FIG. 4) is disengaged in order to allow cocking of the unit. Lying in the cradles, a power unit is longitudinally parallel to the path of the shuttle member, and the pillow 96 of the shuttle aligns with the power unit's thrust rod 28. When the cover is fully opened the leg of the shuttle is pulled to an end of the case to allow room for inserting an uncocked power unit into its cradles. During the course of closing the cover, the leg traverses toward the power units' extended thrust rod until it contacts it. As the cover is further closed, the shuttle leg pushes the thrust rod back into the power unit. This continues until the power unit is cocked and the cover is closed. The cover and the linkage bar combine to provide sufficient mechanical advantage to make cocking a power unit an easy operation. This is an especially important feature for children and the elderly.

The cocking/carrying case is an important element of the system presented herein. It has been found that the coiled spring needs to develop approximately 30 pounds or greater of force in order for the system to sufficiently work on people with a wide range of skin thickness. Therefore a cocking device with mechanical advantage is for all practical purposes necessary.

Referring to FIGS. 9 and 10, a means for injecting medication, i.e., loading an ampule is illustrated. Medication, e.g. therapeutic insulin is available for home health care in generally two types of containers: a standard vial, usually containing 10 ml of the drug, and syringe cartridges containing 1.5 ml or 3 ml of fluid. The ampule loader according to this invention is designed to transfer medication from the conventional syringe cartridges to an ampule. As illustrated it is a pen-size permanent instrument having a small disposable adapter 110 which screws onto the head 112 of a tubular body 114. A cannula 116 in the adapter pierces the conventional rubber stopper 118 of a conventional syringe cartridge 120 which is inserted into a recess 122 defined by the adapter. Adapter and cartridge are then inserted into the tubular loader body 114 and secured in place by screw engagement 124. A base 126 of the loader body defines a threaded opening which engages a jack screw 128. The diameter of the jack screw allows it to extend into the conventionally open base 129 of the syringe cartridge. A shroud 130 affixed to a remote end of the jack screw encloses the jack screw and partially sleeves the rear end of the tubular body. The jack crew is turned by grasping and axially rotating the shroud. The length of the jack screw is sufficient to force syringe cartridge's rubber stopper 132 forward enough to eject substantially all the cartridge's liquid contents through the cannula. At an end of the adapter opposite the syringe cartridge recess 122 is a recess 134 having LUER type threads for mating with the LUER threads 23 on the front end of the ampules. At the base of this recess 134 is a seat 136 defining a centered perforation (not shown) communicating with the cannula. When an ampule is engaged with the adapter, as illustrated in FIG. 10, the frusto-conical protrusion 12 (FIG. 2) of the ampule aligns with and presses against the seat which seals a liquid communication path between the canula and the ampule.

Referring again to FIGS. 9 and 10, to use the ampule loader, an ampule is attached to the adapter by means of the LUER type threads. Then by rotating the jack screw shroud, the syringe cartridge's stopper is forced forward and liquid is forced through the canula and into the ampule, causing the ampule's plunger (13 of FIG. 2) to move back along the scale 18 to a desired dose setting. When the contents of the syringe cartridge are expended (usually about 10 injections) the cartridge and adapter are discarded and a new combination of cartridge and adapter is installed into the loader body. The loader is designed such that the cartridge and the adapter attached to the cartridge stays in the loader body until the medication in the cartridge is used up.

The foregoing description and drawings were given for illustrative purposes only, it being understood that the invention is not limited to the embodiments disclosed, but is intended to embrace any and all alternatives, equivalents, modifications and rearrangements of elements falling within the scope of the invention as defined by the following claims.

I claim:

1. A hand-held, portable apparatus for hypodermically injecting a quantity of liquid comprising:
   (a) a shell defining a chamber for containing the quantity of liquid,
   (b) an orifice communicating with the chamber, a mouth of the orifice being pressed against an injection site whenever an injection is to take place,
   (c) means for converting an applied force to a corresponding pressure applied to the liquid,
   (d) means for coupling the shell to the means for converting an applied force,
   (e) means for accumulating and storing a suitable amount of energy,
   (f) means for manually releasing the stored energy,
   (g) safety means connected between the means for manually releasing the stored energy and the shell for preventing release of the stored energy unless a shell is coupled to said means for converting an applied force, wherein the shell automatically engages the safety means by being coupled to said means for converting an applied force, and
   (h) means for converting the released energy to the applied force, the amount of stored energy being sufficient to produce enough pressure to cause the liquid to leave the chamber via the orifice at such a velocity that it can be hypodermically injected at an injection site.

2. The apparatus according to claim 1 wherein the means for accumulating and storing energy and the means for releasing the stored energy comprises a compressible spring and means for holding the spring in a compressed state, the holding means being responsive to manual actuation.

3. The apparatus according to claim 2 wherein the means for converting the released energy to an applied force comprises a rod axially driven by the released compressed spring.

4. The apparatus according to claim 3 wherein the means for converting an applied force to a corresponding pressure comprises a movable wall of the chamber against which the driven rod acts to forcibly reduce the volume of the chamber.

5. The apparatus according to claim 3 wherein the chamber comprises a hollow cylinder one end of which defines the orifice, and wherein the means for converting an applied force to a corresponding pressure comprises a plunger against which the driven rod acts, the plunger being slidably disposed in the hollow cylinder at an end remote from the orifice.

6. The apparatus according to claim 2 wherein the means for holding the spring in a compressed state comprises a latch which catches an end of the spring when the spring is compressed beyond a certain point and a trigger which releases the latch in response to manual actuation.

7. The apparatus according to claim 6 further comprising an optionally applied means for preventing inadvertent actuation of the trigger.

8. An apparatus for hypodermically injecting a quantity of liquid comprising:
   (a) a liquid container comprising:
      (i) a shell defining a chamber for containing the quantity of liquid,
      (ii) an orifice communicating with the chamber, a mouth of the orifice being pressed against an injection site whenever an injection is to take place, and
      (iii) means for converting an applied force to a corresponding pressure applied to the liquid, and
   (b) a hand-held, portable power unit comprising:
      (i) means for coupling the liquid container and the power unit together in rigid relation,
      (ii) means for accumulating and storing a suitable amount of energy,
      (iii) means for manually releasing the stored energy,
      (iv) safety means connected between the means for manually releasing the stored energy and the liquid container for preventing release of the stored energy unless a liquid container is coupled to the power unit, wherein, the liquid container automatically engages the safety means by being coupled to the power unit, and
      (v) means for converting the released energy to the applied force, the amount of stored energy being sufficient to produce enough pressure to cause the liquid to leave the chamber via the orifice at such a velocity that it can be hypodermically injected at an injection site.

9. The apparatus according to claim 8 wherein the means for accumulating and storing energy and the means for releasing the stored energy comprises a compressible spring and means for holding the spring in a compressed state, the holding means being responsive to manual actuation.

10. The apparatus according to claim 9 wherein the means for converting the released energy to an applied force comprises a rod axially driven by the released compressed spring.

11. The apparatus according to claim 10 wherein the means for converting an applied force to a corresponding pressure comprises a movable wall of the chamber against which the driven rod acts to forcibly reduce the volume of the chamber.

12. The apparatus according to claim 10 wherein the chamber comprises a hollow cylinder one end of which defines the orifice, and wherein the means for converting an applied force to a corresponding pressure comprises a plunger against which the driven rod acts, the plunger being slidably disposed in the hollow cylinder at an end remote from the orifice.

13. The apparatus according to claim 9 wherein the means for holding the spring in a compressed state comprises a latch which catches an end of the spring when the spring is compressed beyond a certain point and a trigger which releases the latch in response to manual actuation.

14. The apparatus according to claim 13 further comprising an optionally applied means for preventing inadvertent actuation of the trigger.

15. A system for hypodermically injecting a quantity of liquid comprising:
   (a) a liquid container comprising:
      (i) a shell defining a chamber for containing the quantity of liquid,
      (ii) an orifice communicating with the chamber, a mouth of the orifice being pressed against an injection site whenever an injection is to take place,
   (b) a power unit comprising:

(i) means for converting an applied force to a corresponding pressure applied to the liquid, (ii) means for coupling the shell to the means for converting an applied force, (iii) means for accumulating and storing a suitable amount of energy, (iv) means for manually releasing the stored energy, (v) safety means connected between the means for manually releasing the stored energy and the liquid container for preventing release of the stored energy unless a shell is coupled to said means for converting an applied force, wherein the shell automatically engages the safety means by being coupled to said means for converting an applied force, and (vi) means for converting the released energy to the applied force, the amount of stored energy being sufficient to produce enough pressure to cause the liquid to leave the chamber via the orifice at such a velocity that it can be hypodermically injected at an injection site, and (c) means for causing said means for accumulating and storing to accumulate said suitable amount of energy.

16. The system according to claim 15 wherein the means for accumulating and storing energy and the means for releasing the stored energy comprises a compressible spring and means for holding the spring in a compressed state, the holding means being responsive to manual actuation.

17. The system according to claim 15 further comprising means for transferring liquid from a conventional syringe cartridge to said chamber.

18. A hand-held, portable apparatus for needleless hypodermic injection of a quantity of liquid comprising:

a shell defining a chamber for containing the quantity of liquid;

an orifice communicating with the chamber, a mouth of the orifice being pressed against an injection site whenever an injection is to take place;

a plunger disposed within the chamber for converting an applied force to a corresponding pressure applied to the liquid;

a power unit including a cylindrical housing defining a longitudinal channel;

a thrust rod disposed in the longitudinal channel for applying said force to the plunger;

means for coupling the shell to the power unit;

a spring disposed within the channel and communicating with the thrust rod, the spring for accumulating and storing a sufficient amount of energy when compressed to produce sufficient pressure to cause the liquid to leave the chamber via the orifice at such a velocity that it can be hypodermically injected at an injection site, wherein the energy is converted to said force by the thrust rod when the spring is released;

a trigger assembly coupled to the spring for manually releasing the stored energy; and a safety interlock assembly, disposed in said coupling means and connected between said trigger assembly and said shell, the safety assembly preventing release of the stored energy by the trigger assembly unless a shell is coupled to the power unit, wherein said shell automatically engages said safety assembly by being coupled to said power unit, thereby allowing release of the stored energy by the trigger assembly.

19. The apparatus according to claim 18 further comprising:

a syringe cartridge;

a liquid transfer unit including a loader assembly with a hollow tubular body adapted to receive the syringe cartridge, the body having a base end defining a threaded opening, a jack screw for rotatably engaging the threaded opening, the jack screw communicating with the syringe cartridge to apply a pressure to liquid within the cartridge when the jack screw is rotated; and a transfer adaptor connected to the tubular body at an end opposite the base end, the adaptor including a cannula which extends into the tubular body and pierces the syringe cartridge, the transfer adaptor including means for coupling to the shell, the orifice of the shell being in communication with the adaptor wherein, as the jack screw is rotated liquid is forced from the syringe cartridge and into the shell.

20. A hand-held, portable apparatus for needleless hypodermic injection of a quantity of liquid comprising:

a shell defining a chamber for containing the quantity of liquid;

a orifice communicating with the chamber, a mouth of the orifice being pressed against an injection site whenever an injection is to take place;

a plunger disposed within the chamber for converting an applied force to a corresponding pressure applied to the liquid;

a power unit including a cylindrical housing defining a longitudinal channel;

a thrust rod disposed in the longitudinal channel for applying said force to the plunger;

means for coupling the shell to the power unit;

a spring disposed within the channel and communicating with the thrust rod, the spring for accumulating and storing a sufficient amount of energy when compressed to produce sufficient pressure to cause the liquid to leave the chamber via the orifice at such a velocity that it can be hypodermically injected at a injection site, wherein the energy is converted to said force by the thrust rod when the spring is released;

a trigger assembly coupled to the spring for manually releasing the stored energy;

a safety interlock assembly, coupled between said trigger assembly and said coupling means, the safety assembly preventing release of the stored energy by the trigger assembly unless a shell is coupled to the power unit; and a carrying case comprising a receptacle wherein the power unit is disposed within the receptacle, the carrying case further comprising a closable lid and means, responsive to the closing of the lid, for engaging the power unit to compress the spring to accumulate said suitable amount of energy.

21. The apparatus according to claim 20 further comprising:

a syringe cartridge;

a liquid transfer unit including a loader assembly with a hollow tubular body adapted to receive the syringe cartridge, the body having a base end defining a threaded opening, a jack screw for rotatably engaging the threaded opening, the jack screw communicating with the syringe cartridge to apply a pressure to liquid within the cartridge when the jack screw is rotated; and a transfer adaptor connected to the tubular body at an end opposite the base end, the adaptor including a cannula which extends into the tubular body and pierces the syringe cartridge, the transfer adaptor including means for coupling to the shell, the orifice of the shell being in communication with the adaptor wherein, as the jack screw is rotated liquid is forced from the syringe cartridge and into the shell.

22. A system for hypodermically injecting a quantity of liquid comprising:
  (a) a liquid container comprising:
    (i) a shell defining a chamber for containing the quantity of liquid,
    (ii) an orifice communicating with the chamber, a mouth of the orifice being pressed against an injection site whenever an injection is to take place,
  (b) a power unit comprising:
    (i) means for converting an applied force to a corresponding pressure applied to the liquid,
    (ii) means for coupling the shell to the means for converting an applied force,
    (iii) a compressible spring;
    (iv) holding means, responsive to manual actuation, for holding the spring in a compressed state;
    (v) safety means connected between the means for manually releasing the stored energy and the liquid container for preventing release of the stored energy unless a shell is coupled to said means for converting an applied force, and
    (vi) means for converting the released energy to the applied force, the amount of stored energy being sufficient to produce enough pressure to cause the liquid to leave the chamber via the orifice at such a velocity that it can be hypodermically injected at an injection site, and
  (c) a carrying case with a lid, said carrying case comprising a closable lid and means, responsive to the closing of the lid, for compressing said spring.

* * * * *